United States Patent
Haider et al.

(10) Patent No.: US 8,401,872 B2
(45) Date of Patent: Mar. 19, 2013

(54) MEDICAL DIAGNOSTIC APPARATUS AND METHOD FOR THE OPERATION THEREOF

(75) Inventors: Sultan Haider, Erlangen (DE); Axel Schreiber, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1123 days.

(21) Appl. No.: 11/603,662

(22) Filed: Nov. 22, 2006

(65) Prior Publication Data

US 2007/0161871 A1    Jul. 12, 2007

(30) Foreign Application Priority Data

Nov. 22, 2005  (DE) .......................... 10 2005 055 657

(51) Int. Cl.
*G06F 19/00* (2006.01)
(52) U.S. Cl. ............... 705/3; 705/2; 705/7.26; 705/7.27
(58) Field of Classification Search .................. 705/2–4, 705/7.26, 7.27
See application file for complete search history.

(56) References Cited

U.S. PATENT DOCUMENTS

| | | | | | |
|---|---|---|---|---|---|
| 4,489,387 | A | * | 12/1984 | Lamb et al. ..................... | 709/237 |
| 4,731,725 | A | * | 3/1988 | Suto et al. ....................... | 706/46 |
| 5,583,758 | A | * | 12/1996 | McIlroy et al. .................. | 705/2 |
| 5,832,455 | A | * | 11/1998 | Hayashi et al. ................ | 705/7.15 |
| 6,029,138 | A | * | 2/2000 | Khorasani et al. ............. | 705/2 |
| 6,149,585 | A | * | 11/2000 | Gray .............................. | 600/300 |
| 6,684,188 | B1 | * | 1/2004 | Mitchell et al. ................ | 705/3 |
| 6,834,285 | B1 | * | 12/2004 | Boris et al. ..................... | 1/1 |
| 6,953,433 | B2 | * | 10/2005 | Kerby et al. ................... | 600/443 |
| 7,247,875 | B2 | * | 7/2007 | Haug et al. ..................... | 250/587 |
| 2002/0085026 | A1 | | 7/2002 | Bocionek et al. | |
| 2003/0050803 | A1 | * | 3/2003 | Marchosky ..................... | 705/3 |
| 2003/0220815 | A1 | * | 11/2003 | Chang et al. ................... | 705/2 |
| 2004/0002884 | A1 | * | 1/2004 | Lenio .............................. | 705/8 |
| 2004/0019482 | A1 | * | 1/2004 | Holub ............................ | 704/231 |
| 2004/0128165 | A1 | | 7/2004 | Block et al. | |
| 2005/0177050 | A1 | | 8/2005 | Cohen | |
| 2005/0177260 | A1 | * | 8/2005 | Schweizerhof et al. ........ | 700/97 |
| 2006/0143057 | A1 | * | 6/2006 | Sadiq ............................. | 705/7 |
| 2007/0038037 | A1 | * | 2/2007 | Fors et al. ..................... | 600/300 |
| 2007/0061176 | A1 | * | 3/2007 | Gress et al. ................... | 705/7 |
| 2007/0179790 | A1 | * | 8/2007 | Leitch et al. ................... | 705/1 |

FOREIGN PATENT DOCUMENTS

WO    WO 2005/051197    6/2005

OTHER PUBLICATIONS

Frank, W. L. (2002). Improved workflow through HIS. Health Management Technology, 23(7), 14-19. Retrieved from http://search.proquest.com/docview/195647929?accountid=14753; comprises the best available Proquest NPL document.*
"Studie zum Aufbau eines Netzwerkes Zwischen Ärzten und Kliniken nach dem Vorbild Virtueller Unternehmen Evaluation der Machbarkeit und Ausarbeitung eines Infrastrukturmodells," Kuhlmann, Publication from University of Augsburg, Oct. 2003.

* cited by examiner

*Primary Examiner* — Gerald J. O'Connor
*Assistant Examiner* — Mark Holcomb
(74) *Attorney, Agent, or Firm* — Schiff Hardin LLP

(57) ABSTRACT

In a method for operation of a medical diagnosis apparatus as well as medical diagnosis-apparatus, with which medical questions are to be answered, the medical questions to be answered is established for each question at least one examination step is determined that is necessary for clarification of the respective medical question, and supplementary information is associated with each examination step, and, using the supplementary information, the examination workflow is determined with the necessary examination steps that are needed to answer all medical questions.

5 Claims, 3 Drawing Sheets

MEDICAL DIAGNOSTIC APPARATUS AND METHOD FOR THE OPERATION THEREOF

BACKGROUND OF THE INVENTION

1. Field of the Invention

The present invention concerns a method for operation of a medical diagnosis apparatus with which specific medical questions can be answered; as well as corresponding a medical diagnostic apparatus.

2. Description of the Prior Art

For the diagnosis of specific medical questions, there are increasingly clear procedural rules for the medical and diagnostic services necessary for this purpose. The examination protocol is linked with the specific questions with regard to the patient and illness, and which questions are to be answered by the examination. Complex diagnosis apparatuses (such as, for example, magnetic resonance tomography (MRT) and computed tomography (CT)) allow the examination personnel to adapt the examination workflow to the question to be answered. Complexities can concern the measurement itself as well as possible post-processing or, documentation steps.

The association of a medical question with a commensurate examination workflow can be difficult and requires a thorough comprehension of the examination method and the illness to be examined. These examinations, however, are often implemented by personnel who do not possess the necessary qualifications to adapt the examination workflow to the question. The same problem results for the doctor who should generate the diagnosis, who sometimes needs assistance in order to select the proper diagnostic procedures and modalities for the current medical questions.

Standardized examination protocols that are predefined at the examination apparatus are known in the prior art. For example, in magnetic resonance tomography a number of imaging sequences are combined into an examination protocol for examination of a predetermined organ. The operator or physician selects the question under the standard protocols. If necessary, these standard protocols are adapted further by expensive, highly-qualified personnel. However, this procedure often leads to unsatisfactory results since medical questions cannot always be directly associated with a standard protocol. For this reason the operating personnel of the diagnosis apparatus must select one or more standard protocols that, however, in total often exceed those needed to answer of the medical question The examination time span is therewith unnecessarily extended, which unnecessarily increases the costs of the examination and which also can entail an additional stress for the examined patient.

Both the number of the medical problems (questions) that should be solved using a specific diagnosis apparatus, and the number of the possible different examination workflows in this diagnosis apparatus, can be very large. For example, questions from all organ regions and many different illnesses can be answered by magnetic resonance tomography, such that there are more than a thousand standard protocols. In these cases medical expertise is required in order to associate a standardized examination workflow with a medical question. Furthermore, there are always combinations of questions for which an optimal examination workflow cannot be defined in advance.

SUMMARY OF THE INVENTION

An object of the present invention is to improve a method for operation of a medical diagnosis apparatus with regard to finding the optimal examination workflow that applies to the patient exposure (stress; load). The examinations (which are sometimes uncomfortable for the patient) should be implemented in an optimized manner, with the costs of the examination being also reduced.

According to a first embodiment of the invention, a method for operation of a medical diagnosis apparatus with which medical questions are to be answered includes the following steps: In a first step, the medical questions to be answered are established. For each question the at least one examination step is subsequently determined that is necessary for clarification of the respective medical question. Furthermore, supplementary information is associated with each examination step. The examination workflow with the necessary examination steps is subsequently determined, this examination workflow being necessary to answer all medical questions. According to the invention, this examination workflow is determined using the supplementary information that is stored regarding each examination step. According to the invention the examination workflow can be automated and optimized using the supplementary information. The examination steps that belong to individual questions can be combined. An optimally less elaborate examination workflow is created that can answer all diagnostic questions.

The examination steps preferably are determined that occur for various diagnostic questions to be clarified, so redundant examination steps are eliminated for the determination of the examination workflow. For example, repeated implementation of individual examination steps can be avoided so the time expenditure of the entire examination can be optimized. The use of various standard protocols that in part exhibit identical examination steps is no longer necessary. If a number of questions are to be answered in the framework of the examination, the examination is thus composed of the sum of the examination steps that were associated with the individual questions, but steps that were selected multiple times are adopted only once. This means that the examination is composed of the smallest superset of the examination steps for all questions.

According to a further embodiment of the invention, after determination of the necessary examination steps the order (sequence) of these necessary examination steps is determined, this determination ensuing using the supplementary information that is associated with each examination step. This means that the supplementary information "order", which can be correspondingly evaluated by a sorter logic, is associated with each examination step. This supplementary information "order" can, for example, state "before contrast agent administration", "after contrast agent administration", "earliest after expiration of a specific time span after contrast agent administration", "first examination step", "after examination step x", etc. The optimal order of the remaining examination steps can be established with this supplementary order information.

Furthermore, the supplementary information that is associated with each examination step can contain, for example, the following information: examination duration, order, prioritization of specific examination steps when alternative examination steps are possible with regard to a question, type of the diagnosis apparatus, etc.

This supplementary information or these attributes are stored for each examination step. For determination of the optimal examination workflow, the corresponding supplementary information of the examination step are then accessed dependent on the parameters to be optimized. For example, the attribute "examination duration" can be associated with each examination step. In order to be able to predict the duration of the entire examination, the examination times of the individual examination steps are added and increased by apparatus-dependent setup times or buffer times. The occupation duration for the diagnosis apparatus can be determined with this prediction and, for example, a free time span for implementation of the measurement can be proposed and this time span can be reserved for the corresponding examination.

Furthermore, it is possible for the diagnosis apparatus to acquire images of the person to be examined in different spatial directions. According to a preferred embodiment, examination parameters that must be adjusted in an examination step can be matched to one another for identical spatial directions. For example, for magnetic resonance tomography apparatuses an identical volume coverage (meaning a determined field of view with a determined layer thickness) can be selected for the identical orientation.

Some questions can be answered with various alternative examination steps. Hemorrhaging confirmation in the brain as an example in magnetic resonance tomography which is possible using a B0 image for a diffusion measurement or with the aid of a T2*-weighted FLASH measurement. The decision of which examination step should then actually be selected for an examination is supported by the supplementary information "prioritization" of the alternative examination steps. Such prioritizations can be, for example: "which alternative is the most advantageous", "use alternative 1 when this examination step is already required by a different question for this examination" and/or "this alternative can additionally be measured when also reasonable for another question", etc. Other prioritization information naturally is possible. Furthermore, it is also possible for a question to be answered by different diagnosis apparatuses. In this case, the supplementary information also includes information about the diagnosis apparatus to be used. Dependent on the present medical indications, the diagnosis apparatus or the diagnosis apparatuses can then be selected using this supplementary information "apparatus type". Based on the steps that are necessary overall, a proposal can then be automatically output as to the order that a patient should be examined at which diagnosis apparatus. The administration of a number of medical diagnosis apparatuses thus can be simplified since the occupation time as well as the necessary method steps can be automatically associated with the various diagnosis apparatuses.

The invention furthermore concerns a medical diagnosis apparatus for examination of an examination subject the medical diagnosis apparatus having a signal acquisition unit for acquisition of the signal with which medical questions should be answered. For example, with an acquired signal an image can then be obtained with which the medical question can be answered. Furthermore, a storage unit is provided that contains a number of data sets, each data set containing the following components:

at least one medical question,
the examination steps that are necessary or possible for clarification of this question.

In addition to supplementary information with regard to each examination step, supplementary information is also stored which can (as mentioned above) include information about the examination duration, order, prioritization, type of the diagnosis apparatus. Furthermore, a control unit is provided that optimizes the examination workflow using the supplementary information, meaning that it determines the necessary examination steps that are necessary to answer all medical questions. If a number of different medical diagnosis apparatuses are present, an administration system can also include the above components, and the administration system can additionally establish at which diagnosis apparatus which examination step is implemented

DESCRIPTION OF THE DRAWINGS

FIG. 3 shows an association of the medical question with the necessary examination steps and the supplementary information associated there with.

FIG. 4 shows an example of the storage of the supplementary information regarding a work step.

DESCRIPTION OF THE PREFERRED EMBODIMENTS

Figure 1:
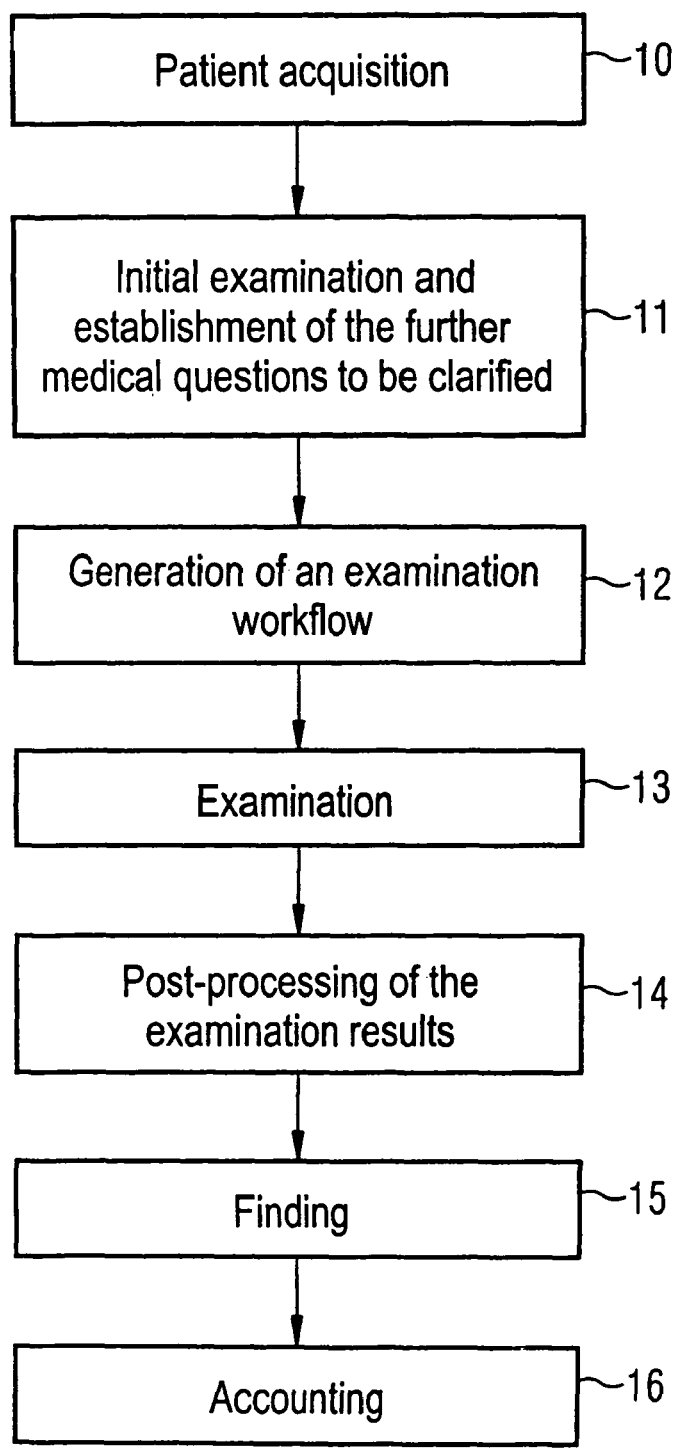
FIG. 1 is a flow chart that shows the workflow of a diagnostic examination.

FIG. 1 shows the typical method steps that occur in the generation of a diagnosis with the aid of a diagnostic apparatus. For example, in a first step 10 the patient acquisition can ensue with storage of the patient data. In an initial examination it is subsequently established which diagnostic questions should be answered (step 11). Finally the examination workflow is then established in a step 12. In this step 12 the examination workflow is inventively optimized using the supplementary information, as is later explained in detail. In step 13 the examination is finally implemented before the examination results are post-processed in a step 14. In a step 15 the results are finally assessed and possibly invoiced in a step 16.

Figure 2:
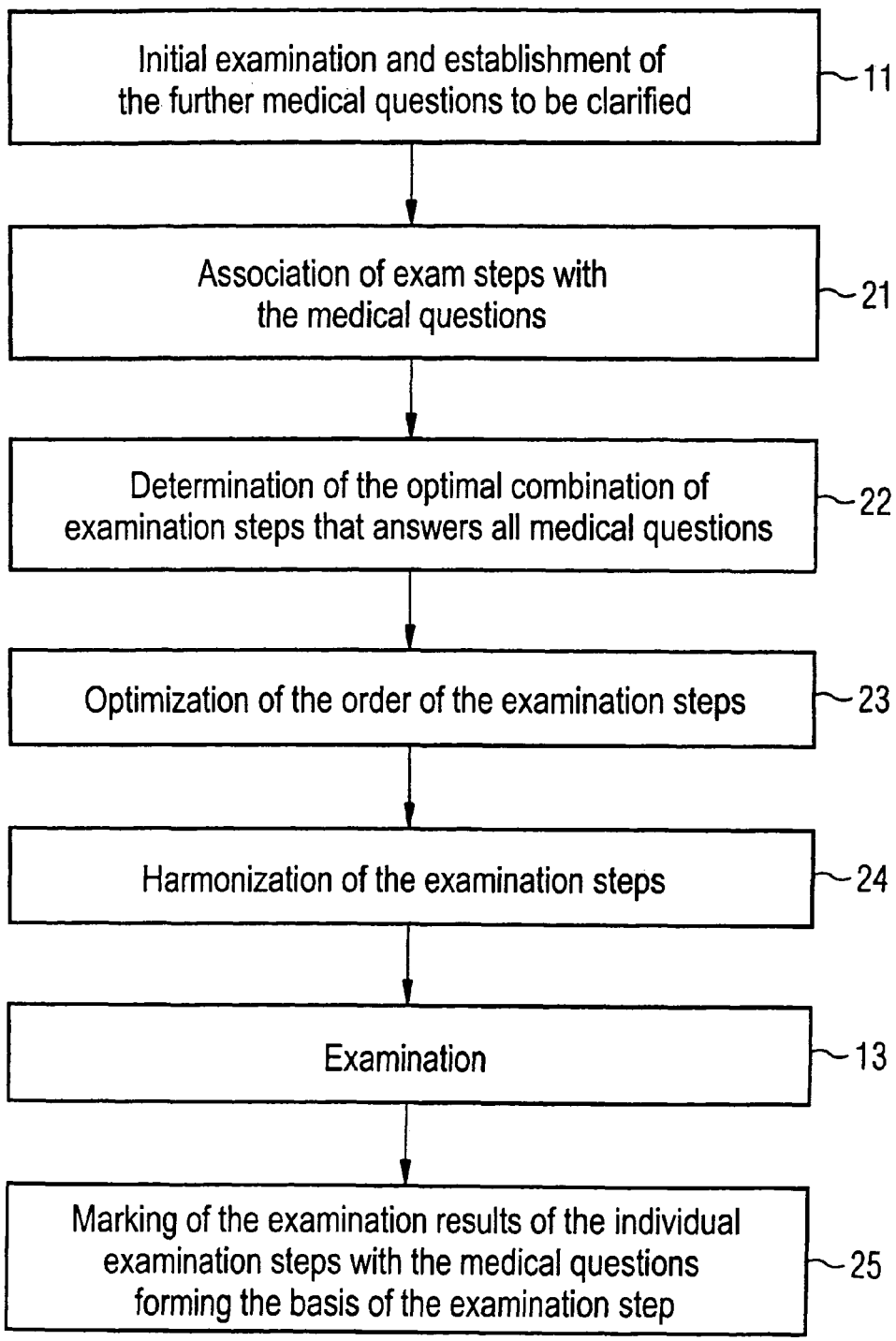
FIG. 2 is a flow chart that shows the generation of an automatic examination workflow in detail.

FIG. 2 shows in detail and in an optimized manner how the examination workflow can be automatically generated. After the initial examination already shown in FIG. 1 and the establishment of the further diagnostic questions to be clarified in step 11, the examination step or steps for each diagnostic question are determined that are necessary for clarification of the respective medical question (step 21). In a step 22 the optimal combination of the examination steps is subsequently determined that answers all medical questions. For example, examination steps occurring twice are hereby eliminated.

In step 23 the order of the remaining examination steps is subsequently optimized (step 23), with these examination steps being harmonized (i.e. adapted to one another) (step 24). The actual examination, as shown in FIG. 1 in step 13, can subsequently be implemented. Furthermore, in a step 25 the examination results of the individual examination steps can optimally be marked with the questions that form the basis of the examination step.

Figures 3, 4:
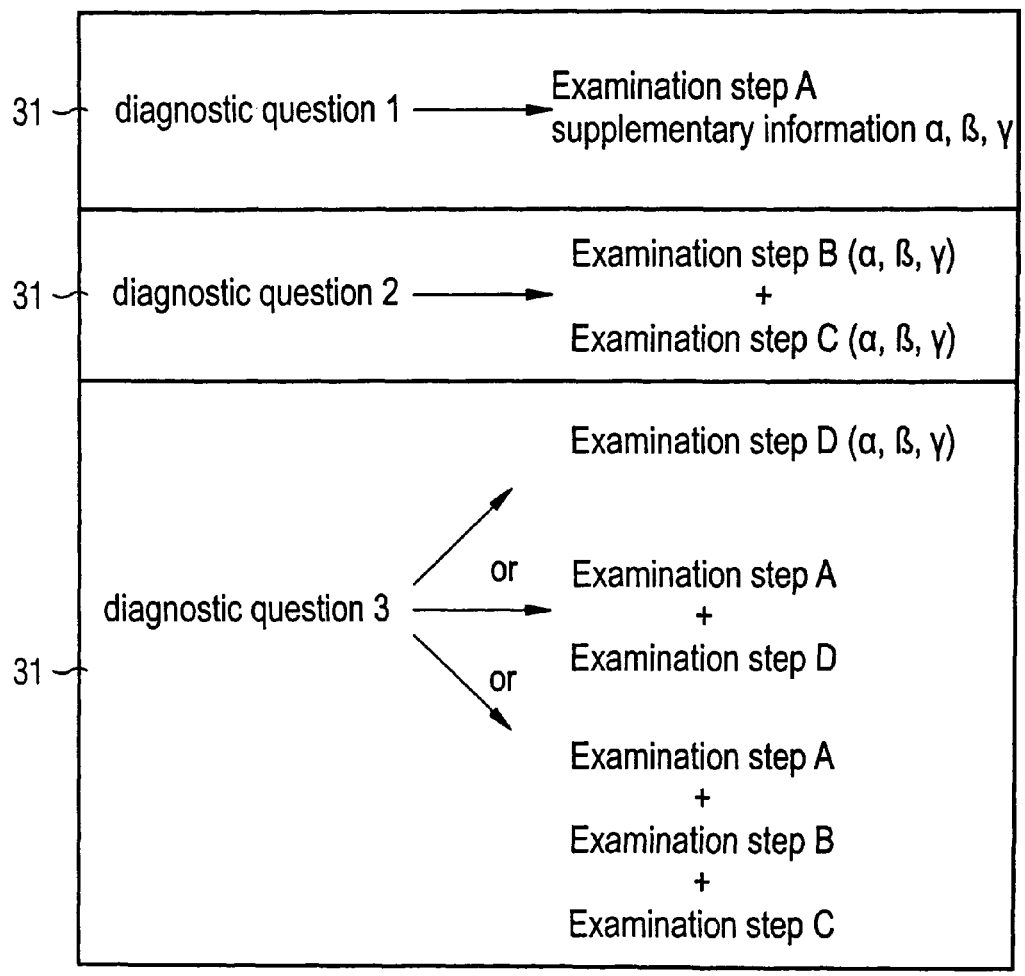

The association of the medical question with the examination step or steps and the supplementary information is exemplarily shown in FIG. 3. The table from FIG. 3 contains a number of data sets 31. Each data set represents a medical question and the examination step associated with this. In addition to the examination step, the supplementary information are stored (as shown in FIG. 4) that establish, for example, the order of a number of examination steps and, contain information about which medical or diagnostic questions are answered. Furthermore, the information of the examination duration can be specified as well as the prioritization in the event that alternative examination steps are possible.

As shown in FIG. 3, an examination step A is necessary to answer the medical question 1, the examination steps B and C are necessary to answer the question 2. Either the examination step D or the examination steps A+B or the examination steps A+B+C are executed for clarification of the question 3. If the diagnostic questions 1, 2 and 3 should now be clarified, possible examination workflows result: examination step A+examination step B+examination step C+examination step D. The workflow examination step A+B+C+A+D is likewise possible, or the workflow A+B+C+A+B+C. When the superfluous examination steps are now suppressed, the possible workflows A+B+C+D and A+B+C are obtained. The examination workflow that is most bearable for the patient, or, the most economical examination workflow, can then be selected from these three possible workflows. In the present case, for example, this would be the examination workflow A+B+C. The optimal order of the examination can then be subsequently determined by the supplementary information "order". The optimal order can be: examination step B before examination step C before examination step A.

As can be seen from table 3, the examination workflow contains the sum of the examination steps that were associated with the individual questions, but examination steps occurring multiple times (in the example from FIG. 3 the examination steps A and B occurring twice in the answer of the questions 1, 2 and 3) are eliminated.

Furthermore, the information about the relevance of the question can be given with the result of the respective examination step and be stored with this, for example in the header of an image series. This information enables effective data administration. It is possible to select the correct images for a post-processing and, if applicable, to automatically load them into the correct applications. It is also possible to offer this information for the findings, for example sorted according to the question to be answered.

In summary, the invention enables an optimization of an examination process with which all superfluous examination steps are eliminated and given which the examination personnel are supported in the selection of the correct diagnostic modalities.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computerized method for operating a medical diagnostic apparatus to answer medical questions, comprising the steps of:
   establishing multiple medical questions about a patient to be answered contemporaneously with each other by implementing an examination workflow on a patient, and entering said multiple medical questions in computer-readable form into a computer;
   in said computer, for each of said multiple medical questions, automatically electronically determining at least one examination step, from among a plurality of alternative examination steps, that is necessary to answer the respective medical question, and automatically electronically associating prioritization information with each of said alternative examination steps that defines at least one condition that, when present, gives the examination step associated therewith a priority over others of said alternative examination steps;
   in said computer, automatically determining whether said at least one condition is present and using the prioritization information to automatically electronically compile said examination workflow so as to encompass all examination steps that are necessary to contemporaneously answer all of said medical questions while automatically eliminating, based on said prioritization information, subjecting said patient to any redundant examination steps in said examination workflow; and
   emitting a signal representing said examination workflow without any redundant steps therein at an output of the computer.

2. A method as claimed in claim 1 comprising, using said prioritization information, automatically electronically determining a sequence of said examination steps in said workflow.

3. A method as claimed in claim 1 comprising also associating supplementary information with each examination alternative step selected from the group consisting of examination duration, and type of diagnostic apparatus to be used in the examination step.

4. A method as claimed in claim 1 comprising automatically electronically using said prioritization information to determine a diagnostic apparatus, from among a plurality of available diagnostic apparatuses, to use in the respective examination steps.

5. A computerized apparatus for operating a medical diagnostic apparatus to answer medical questions, comprising:
   a processor;
   an input unit connected to said processor configured to enter into said processor in a form readable by said processor, multiple medical questions about a patient to be answered contemporaneously with each other by implementing an examination workflow on a patient;
   a storage unit accessible by said processor containing a plurality of data sets, each data set comprising a medical question and alternative examination steps necessary for answering the medical question, together with prioritization information that is stored associated with each of said alternative examination steps that defines at least one condition that, when present, gives the examination step associated therewith a priority over others of said alternative examination steps;
   said processor being configured, for each of said medical questions, to automatically retrieve the data set therefor from said storage unit, together with the associated prioritization information;
   said processor being configured to determine said at least one condition is present and to use the prioritization information and the data set retrieved from the storage unit to automatically compile said examination workflow so as to encompass all examination steps that are necessary to contemporaneously answer all of said medical questions, while automatically eliminating, based on said prioritization information, subjecting said patient to any redundant examination steps in said examination workflow; and
   said processor being configured to emit an output signal at an output of the processor representing said examination workflow without any redundant steps therein.

* * * * *